United States Patent [19]

Nappholz et al.

[11] 4,448,197

[45] May 15, 1984

[54] HEART PACER END-OF-LIFE DETECTOR

[75] Inventors: Tibor A. Nappholz, Drummoyne; David K. Money, Pennant Hills; Stephen Swift, Hornsby; Ronald C. Bradbury, Marsfield, all of Australia

[73] Assignee: Telectronics Pty. Ltd., Lane Cove, Australia

[21] Appl. No.: 401,013

[22] Filed: Jul. 22, 1982

[51] Int. Cl.³ .............................................. A61N 1/36
[52] U.S. Cl. .............................................. 128/419 PT
[58] Field of Search .................. 128/419 PT, 419 PG, 128/419 PS

[56] References Cited

U.S. PATENT DOCUMENTS

| | | | |
|---|---|---|---|
| 3,656,487 | 4/1972 | Gobeli | 128/419 PG |
| 3,759,266 | 9/1973 | Lee | 128/419 PS |
| 3,774,619 | 11/1973 | Goldberg | 128/419 PT |
| 3,789,854 | 2/1974 | Lee | 128/419 PG |
| 3,901,247 | 8/1975 | Walmsey | 128/419 PG |
| 4,102,346 | 7/1978 | Fulker | 128/419 PS |

Primary Examiner—William E. Kamm
Assistant Examiner—Mitchell J. Shein
Attorney, Agent, or Firm—Gottlieb, Rackman & Reisman

[57] ABSTRACT

A heart pacer in which the magnitude of the end-of-life test current source is programmable. This effectively allows the physician to program the condition which will control a switch-over to end-of-life operation. It also allows the physician to override end-of-life operation after it initially takes place following a failing of the end-of-life test. The pacer also includes an additional end-of-life test involving the continuous monitoring of the supply potential and a switch-over to end-of-life operation should the pacer powering potential momentarily fall below a threshold level.

11 Claims, 1 Drawing Figure

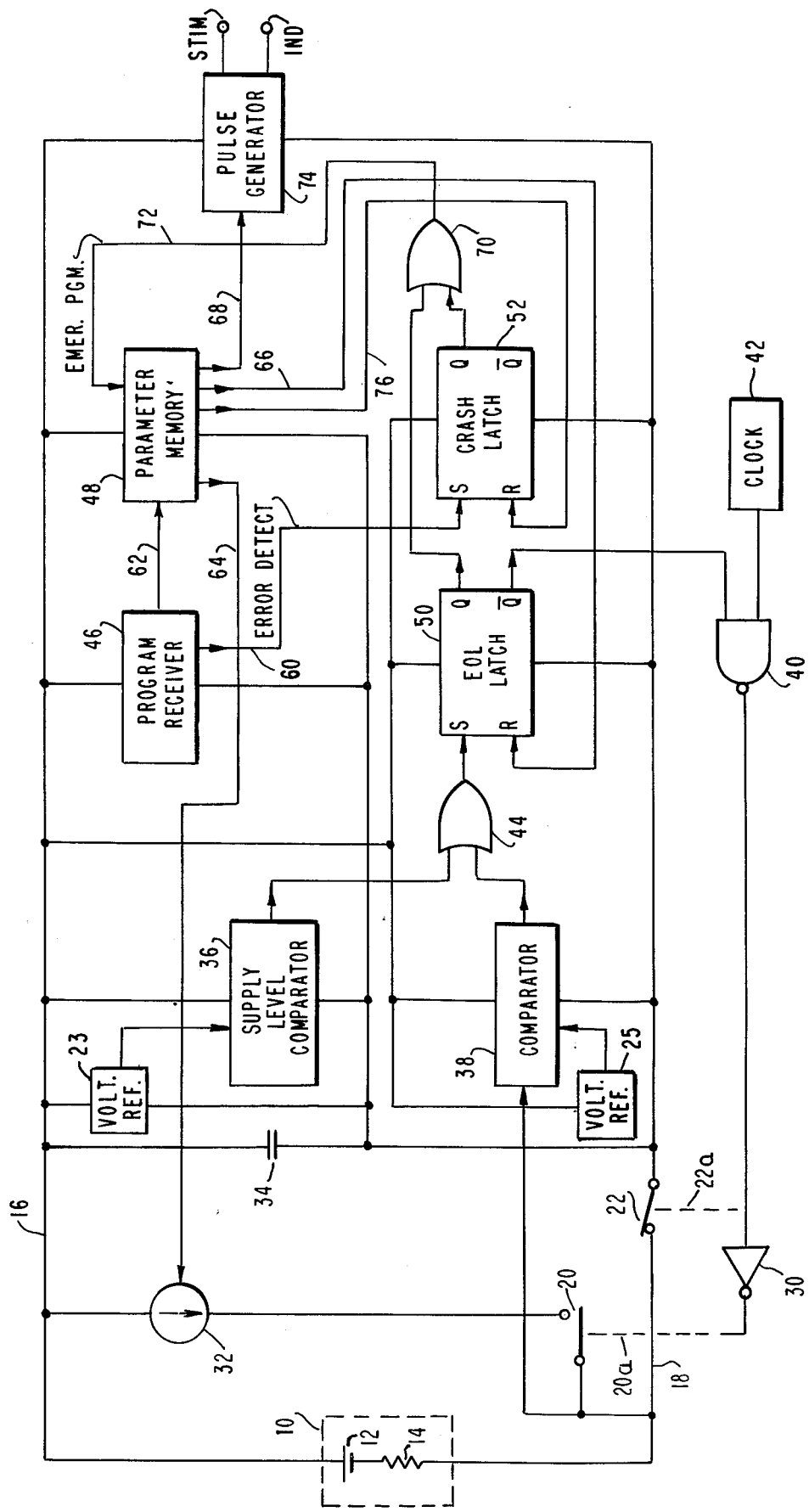

HEART PACER END-OF-LIFE DETECTOR

DESCRIPTION

This invention relates to implantable heart pacers, and more particularly to the operation of such a pacer toward the end of life of its battery.

A conventional implantable programmable heart pacer includes a mechanism for receiving externally-generated programming pulses and appropriately setting parameter values which control the pacer operation. Typical parameter values which may be programmed are pacer pulse width, pacing rate, input sensitivity, and even the pacer mode of operation, e.g., whether the pacer is operated in the synchronous or inhibit mode.

A conventional implantable heart pacer also includes a mechanism for determining when the battery is approaching its end of life. One such scheme involves momentarily disconnecting the battery from the pacing circuitry and causing the current from a predetermined, fixed source to flow through the battery. The voltage across the battery in such a case is necessarily equal to the open-circuit potential of the battery minus the voltage drop across the internal battery impedance. The battery impedance increases as the cell depletes, and if the total potential across the battery when the fixed current flows through it is less than a threshold level, a latch is set to indicate that the pacer requires replacement. The setting of the latch controls the use of "emergency program" parameter values. Typically, the pacer will operate at a lower rate in order to conserve the battery. The physician is able to determine the end-of-life condition when he observes that the pacer is operating in accordance with the emergency program parameter values.

There are three problems with this general prior art approach. The first relates to the overriding effect of the end-of-life detector. Once an end-of-life condition is detected, the pacer automatically operates in the "emergency mode". Even should the physician attempt to re-program the pacer, the end-of-life detector will still detect the run-down condition of the battery and it will immediately re-program the pacer to the emergency parameter values. However, in many cases once the physician is alerted to the fact that the pacer needs replacement, there is really no need for the pacer to operate in a mode which minimizes the current drain. The battery usually has sufficient capacity to power the pacer, even if programmed to draw a large current, for a time interval which is sufficient to allow orderly replacement of the unit.

The second problem concerns the current source which is used for end-of-life detection. The reason that the battery impedance, and the manner in which it increases with age, is important in the first place is that the voltage furnished to the pacing circuitry is not the open-circuit battery potential but rather this potential minus the voltage drop across the internal impedance of the battery. As the impedance increases, the potential furnished to the pacing circuitry decreases, and if the potential falls too low the pacer may malfunction. A particularly sensitive sub-system in this regard is the memory which stores the programmed parameter values. If the potential drops too low, the contents of memory may be undefined.

The use of a fixed test current source assumes that there is some minimum potential which should trigger end-of-life operation, and that this potential is a direct function of the battery impedance. In reality, however, this is not the case. The potential furnished by the battery is a function not only of the open-circuit potential and the battery impedance, but also the current which flows through the battery. The larger the current, the lower the powering potential. There is usually a filter capacitor placed across the battery terminals for filtering transients so that even when current surges are required, the powering potential remains relatively constant. The powering potential is thus a function of the average current drawn from the battery. Depending on the parameter values programmed by the physician, the average current drawn from the battery may vary appreciably. Obviously, the lower the pacing rate, the less current which is drawn. Conventional fixed current sources which are used to detect end of life ignore the fact that it is not only battery impedance which is important in determining when the parameter values should be changed automatically so as to conserve the battery. It is just as important to take into account the average current drawn from the battery as it is to take into account the battery impedance, in deciding whether end-of-life operation is called for. Prior art end-of-life detectors generally ignore the current factor; the use of a fixed test current source implies that battery impedence is the only consideration in determining end of life.

The third problem with prior art end-of-life detectors concerns the test procedure itself. Despite the use of a capacitor across the battery for filtering purposes, the potential furnished to the pacing circuitry does change as a function of time. The largest current drawn from the battery occurs following the generation of a pacing pulse when the capacitor or capacitors in the output stage have to be recharged. The large current which flows from the battery may result in a significant drop in the powering potential. While the use of a current-source test may provide an end-of-life indication based upon "average" conditions, instantaneous conditions are also important. A momentary drop in the powering potential may be sufficient to erase the memory and cause other malfunctions. Thus it sometimes happens that the pacer malfunctions despite the fact that the end-of-life test does not detect an end of life. Under such conditions, it is important that the pacer automatically switch to operate in accordance with the emergency parameter values so that the physician can at least be informed that replacement is necessary.

It is a general object of our invention to provide a heart pacer which overcomes the above-described shortcomings of prior art end-of-life test circuits.

Briefly, in accordance with the principles of our invention and in the illustrative embodiment thereof, we provide a programmable current source for use in the end-of-life test. The magnitude of the current used in the test may be programmed to one of several (e.g., three) values just as other parameter values may be programmed by the physician. Once an end-of-life condition is detected, the physician can re-program the pacer to operate with other than emergency parameter values. As part of the programming, the magnitude of the test current can be decreased. What this means is that all subsequent end-of-life tests will result in a higher potential being detected due to the lower voltage drop across the internal battery impedance. Thus once the test current is decreased in magnitude, the pacer will not be "locked in" to operate with emergency parameter values despite subsequent programming by the physician. The physician already knows that replacement is necessary, and until the replacement is actually effected the patient's heart still may be paced at the desired rate.

This same technique of programming the test current source allows the physician to assert control over the initial end-of-life determination. In the case of a pacer which draws a relatively low average current from the battery, a higher internal battery impedance may be tolerated. In other words, the battery impedance may be allowed to increase to a greater extent before the pacer is switched to operate with emergency parameter values. The physician can control this by programming a lower test current. The use of a lower test current will not result in the powering potential dropping below the threshold value during the test until the internal battery impedance becomes greater. Thus the use of a programmable test current source not only allows the physician to override end-of-life operation, but it also allows him to effectively program the value of battery impedance which will trigger end-of-life detection in the first place.

The use of a programmable test current, however, does not solve the third problem discussed above, namely, that of the powering potential momentarily falling below the minimum safe value due to instantaneous current surges—even though the battery impedance may be below that value which triggers end-of-life detection. For this reason we provide a second test mechanism which continuously compares the instantaneous supply level with a threshold value. If the powering potential ever drops below this threshold level, the pacer automatically switches to its emergency mode of operation. In this manner the physician can be apprised of the fact that pacer replacement is necessary. The supply-level test is independent of the periodic current test; an end-of-life condition can be detected by either of two independent test circuits.

Further objects, features and advantages of our invention will become apparent upon consideration of the following detailed description in conjunction with the drawing which depicts in block diagram form the illustrative embodiment of our invention.

Block 10, shown in dashed outline, represents the pacer battery. The battery can be represented as a potential source 12 and an internal impedance 14. The potential difference which actually appears across busses 16 and 18 is equal to the potential of source 12 minus the voltage drop across the internal impedance 14. Busses 16 and 18 are connected to the various sub-systems in the pacer for powering them; the sub-systems themselves are shown as blocks since they are all standard devices well known in the art.

The critical element in any heart pacer is the pulse generator, shown as block 74 in the drawing. The pulse generator is connected over two leads to the stimulating and indifferent electrodes, and the generator includes timing and logic circuits for determining when a stimulating pulse is required and for generating the pulse. The pulse generator itself is shown in the drawing only in the form of a block inasmuch as its operation is not required for an understanding of the present invention. All that must be understood is that the operation of the pulse generator is controlled by parameter values which are stored in memory 48, the parameter values being extended to the pulse generator as shown symbolically by bus 68. The parameter values themselves are ordinarily stored in memory 48 under control of program receiver 46. This device detects externally generated pulses, decodes them, and controls the storage of the parameter values in memory 48 by transmitting appropriate signals over bus 62. The program receiver and parameter memory are shown only in block form inasmuch as the design of such circuits are well known to those skilled in the pacer art.

As is also standard in the art, program receiver 46 checks that the externally generated pulses are received in a proper format; without such a check, an error in transmission could result in improper setting of the parameter values. In the event of the detection of a transmission error, ERROR DETECT conductor 60 is pulsed high to set crash latch 52. The Q output of the latch goes high and a positive potential is extended through OR gate 70 to EMERGENCY PROGRAM conductor 72. A positive potential on this conductor, which is connected to a second input of parameter memory 48, causes emergency parameter values to be stored in the memory independent of the operation of program receiver 46. In this way, by monitoring the pacer operation, the physician can determine that the parameter values were not set as he desired them to be. The emergency parameter values are those associated with an end-of-life condition. Typically, the parameter values are such that minimal current is drawn from the battery so as to prolong its life.

End-of-life latch 50 operates in a similar manner to control the storage of the emergency parameter values in memory 48 when an end-of-life condition is detected. The setting of latch 50 causes its Q output to go high and a positive potential to be extended through OR gate 70 to appropriately program memory 48. The mechanism for setting latch 50 is conventional (except for the manner in which current source 42 can be programmed, as will be described below).

Switches 40 and 42 are normally in the respective positions shown in the drawing. With end-of-life latch 50 in its normal reset condition, its $\bar{Q}$ output is high to enable gate 40. The output of clock 42 is normally low so that the gate output is normally high. Switch 42 is held closed by a high potential at the output of gate 40, as shown symbolically by dashed lines 22a. Inverter 30 applies a low potential at its output to hold switch 20 open, as shown symbolically by dashed line 20a. With the switches in their normal positions as shown, no current can flow from source 32, and the negative terminal of the battery, connected to bus 18, has its potential extended through switch 22 to the various blocks which are powered by the battery.

Every few seconds, the output of clock 42 goes high for about one millisecond. When the output of gate 40 goes low, switch 22 opens and switch 20 closes. It is at this time that the negative terminal of the battery is disconnected from the various pacer circuits which are powered. These circuits still operate, however, because of the provision of conventional filter capacitor 34. The charge stored on this capacitor is sufficient to power the pacer for the one millisecond or so that switch 22 is open. (Instead of automatically performing the test under control of clock 42, it is possible, as is known in the art, to perform the test only under external program control. In either case, however, the current source is only selectively connected across the battery—whenever the test is to be performed.)

With switch 20 closed during the test cycle, current from source 32 flows through battery 10. Were no current to flow from current source 32, the potential difference across busses 16 and 18 would equal the open-circuit potential represented by source 12. But with current flowing through the battery, the potential difference is less, by the value of the potential drop across internal impedance 14. Comparator 38 effectively compares the potential difference across busses 16 and 18 with a reference level furnished by voltage reference source 25. If the potential difference falls below the reference level, as it will for large internal battery impedances, the output of the comparator goes high. The positive potential extended through OR gate 44 sets latch 50. As described above, this results in the storage in memory 48 of the emergency parameter values. At the same time, the $\overline{Q}$ output of the latch goes low and holds the output of gate 40 high permanently. This causes switches 20 and 22 to remain in their normal positions independent of the output of clock 42 going high. Once an end-of-life condition has been detected, there is no longer a need to test the battery impedance.

Unlike the prior art in which current source 32 has a fixed level, in accordance with the principles of our invention the level of current source 32 can be programmed. One of the parameter values stored in memory 48 is the magnitude of the current source, the value being extended over bus 64 to the current source for controlling the magnitude of the test current. This control allows the physician to determine the value of impedance 14 which will result in the setting of latch 50. As described above, when the average current drawn by the pacing circuitry is low, a larger internal battery impedance can be tolerated. Since comparator 38 responds to a predetermined potential difference across busses 16 and 18, the comparator can be made to detect an end-of-life condition represented by a higher internal battery impedance simply by using a lower-magnitude test current. The physician adjusts the magnitude of the test current in accordance with the other parameter values which he programs; in this way, for a low average current drain (e.g., a low pacing rate), the physician will not be informed that pacer replacement is necessary until the battery impedance increases more than it otherwise would for latch 50 to be set. In effect, the physician is now able to program an end-of-life test value just as he can program other parameter values.

While this gives the physician control over the value of battery impedance which will trigger end-of-life operation, in and of itself the arrangement is not sufficient for overriding the emergency parameter values after latch 50 is first set. As described above, it would be beneficial to allow the physician to re-program the pacer for "normal" operation even though an end-of-life condition has been detected; the physician knows that a replacement is necessary, and under normal circumstances the battery will still have sufficient capacity to allow normal operation to proceed for quite some time even though the internal impedance has reached the threshold level. In order to allow such re-programming, however, latch 50 must somehow be reset.

It should first be noted that following an error in transmission and the setting of crash latch 52, this latch must be reset in order for another attempt to program the pacer to have any chance of succeeding. For this reason, the storage of any set of parameter values in memory 48 results in a positive pulse being applied to conductor 76 for resetting latch 52. But as far as latch 50 is concerned, it is not critical that the latch be allowed to reset following the detection of an end-of-life condition; the pacer requires replacement and the emergency parameter values may be used until the replacement is effected. However, the physician, once he is alerted to the fact that a replacement is necessary, may decide that the pacer should operate with "normal" parameter values until the replacement is effected. For this reason, one of the parameter values which the physician may program is an end-of-life "reset". When such a reset "parameter value" is programmed, a positive pulse is applied to conductor 66 for resetting latch 50. In this way, the other parameter values which are being programmed may take effect.

Of course, all of this would be to no avail were an end-of-life condition to be detected a few seconds later when the end-of-life test is performed once again with the opening of switch 22 and the closing of switch 20. To prevent the next test from setting latch 50 once again, the physician should program current source 32 to have a lower magnitude at the same time that he programs the "normal" parameter values. The use of a smaller test current will result in a higher potential difference across busses 16 and 18 so that comparator 38 will not result in the setting of latch 50 once again.

As described above, the standard type of end-of-life test is designed to ensure that the average current which can be drawn from the battery (as determined by the battery impedance) exceeds some predetermined minimum value. But there is still the danger of a large momentary drop in supply potential due to some transient condition, resulting perhaps in erasure of parameter memory 48. To guard against such a contingency, continuously-operating supply level comparator 36 is provided. This device simply compares the potential difference across busses 16 and 18 with a threshold level furnished by voltage reference source 23, with the output of the comparator going high if the potential difference across the busses falls too low. The threshold level, of course, is higher than the potential difference which would result in erasure of the memory; the idea is to control a switch to the emergency parameter values, so that less current is drawn from the battery, before the memory-erasure point is actually reached. When the output of comparator 36 goes high, the positive potential is extended through OR gate 44 to set latch 50, following which the operation of the pacer is the same as that which ensues when the latch is set with the output of comparator 38 going high.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A programmable heart pacer comprising a power source, a pulse generator for generating pacing pulses, means for storing externally-generated parameter values and for controlling the operation of said pulse generator in accordance with the stored parameter values, and means for detecting the approach of the end of life of said power source and in response thereto for storing in said storing means predetermined parameter values, said detecting means including means for selectively connecting a test current source across said power source and means for comparing with a reference value the potential across said power source when a test current flows therethrough, characterized by said storing means further storing a variable test current source magnitude parameter value, and means for controlling the magnitude of said test current source in accordance with the stored test current source magnitude parameter value.

2. A programmable heart pacer in accordance with claim 1 further including means responsive to an initial operation of said detecting means for latching an end-of-life indication to thereafter control operation of said pulse generator in accordance with said predetermined parameter values, and means responsive to an externally-generated signal for resetting said latching means.

3. A programmable heart pacer in accordance with claim 2 wherein said detecting means further includes continuously operating means for detecting a momentary decrease in the potential of said power source below a predetermined threshold level.

4. A programmable heart pacer in accordance with claim 2 wherein said detecting means further includes means for operating independently of the operation of said test current source to detect a momentary decrease in the potential of said power source below a predetermined threshold level.

5. A programmable heart pacer in accordance with claim 1 wherein said detecting means further includes continuously operating means for detecting a momentary decrease in the potential of said power source below a predetermined threshold level.

6. A programmable heart pacer in accordance with claim 1 wherein said detecting means further includes means for operating independently of the operation of said test current source to detect a momentary decrease in the potential of said power source below a predetermined threshold level.

7. A programmable heart pacer comprising a power source, a pulse generator for generating pacing pulses, means for storing externally-generated parameter values and for controlling the operation of said pulse generator in accordance with the stored parameter values, and means for detecting the approach of the end-of-life of said power source and in response thereto for storing in said storing means predetermined parameter values, characterized by said storing means further storing a variable parameter value indicative of an end-of-life condition, and means for controlling said detecting means to operate in accordance with the stored parameter value indicative of an end-of-life condition.

8. A programmable heart pacer in accordance with claim 7 further including means responsive to an initial operation of said detecting means for latching an end-of-life indication to thereafter control operation of said pulse generator in accordance with said predetermined parameter values, and means responsive to an externally-generated signal for resetting said latching means.

9. A programmable heart pacer comprising a power source, a pulse generator for generating pacing pulses, means for storing externally-generated parameter values and for controlling the operation of said pulse generator in accordance with the stored parameter values, and means for detecting the approach of an end-of-life condition of said power source and in response thereto for storing in said storing means predetermined parameter values, said detecting means including means for selectively connecting a test current source across said power source and means for comparing with a reference value the potential across said power source when a test current flows therethrough, characterized by means responsive to an initial operation of said detecting means for latching an end-of-life indication to thereafter control operation of said pulse generator in accordance with said predetermined parameter values, and means responsive to an externally-generated signal for resetting said latching means and preventing subsequent operation of said detecting means for the same condition of said power source.

10. A programmable heart pacer in accordance with claim 9 wherein said detecting means further includes continuously operating means for detecting a momentary decrease in the potential of said power source below a predetermined threshold level.

11. A programmable heart pacer in accordance with claim 9 wherein said detecting means further includes means for operating independently of the operation of said test current source to detect a momentary decrease in the potential of said power source below a predetermined threshold level.

* * * * *